(12) United States Patent
Butler et al.

(10) Patent No.: US 8,314,282 B2
(45) Date of Patent: Nov. 20, 2012

(54) PROCESS FOR PRODUCTION OF ETHYLBENZENE FROM TOLUENE AND METHANE

(75) Inventors: James R. Butler, Spicewood, TX (US); Joseph E. Pelati, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 13/290,211

(22) Filed: Nov. 7, 2011

(65) Prior Publication Data
US 2012/0059206 A1    Mar. 8, 2012

Related U.S. Application Data

(62) Division of application No. 12/047,953, filed on Mar. 13, 2008, now Pat. No. 8,076,527.

(51) Int. Cl.
C07C 2/64 (2006.01)
C07C 5/09 (2006.01)
(52) U.S. Cl. ......... 585/899; 585/943; 585/452; 585/323
(58) Field of Classification Search .................. 585/899, 585/943, 452, 323
See application file for complete search history.

(56) References Cited

U.S. PATENT DOCUMENTS
4,956,327 A * 9/1990 Erekson et al. ............... 502/216
* cited by examiner

*Primary Examiner* — Thuan D Dang

(57) ABSTRACT

A process for making ethylbenzene and/or styrene by reacting toluene with methane is disclosed. In one embodiment the process can include reacting toluene with methane to form a product stream comprising ethylbenzene and further processing the ethylbenzene to form styrene in an existing styrene production facility.

8 Claims, 2 Drawing Sheets

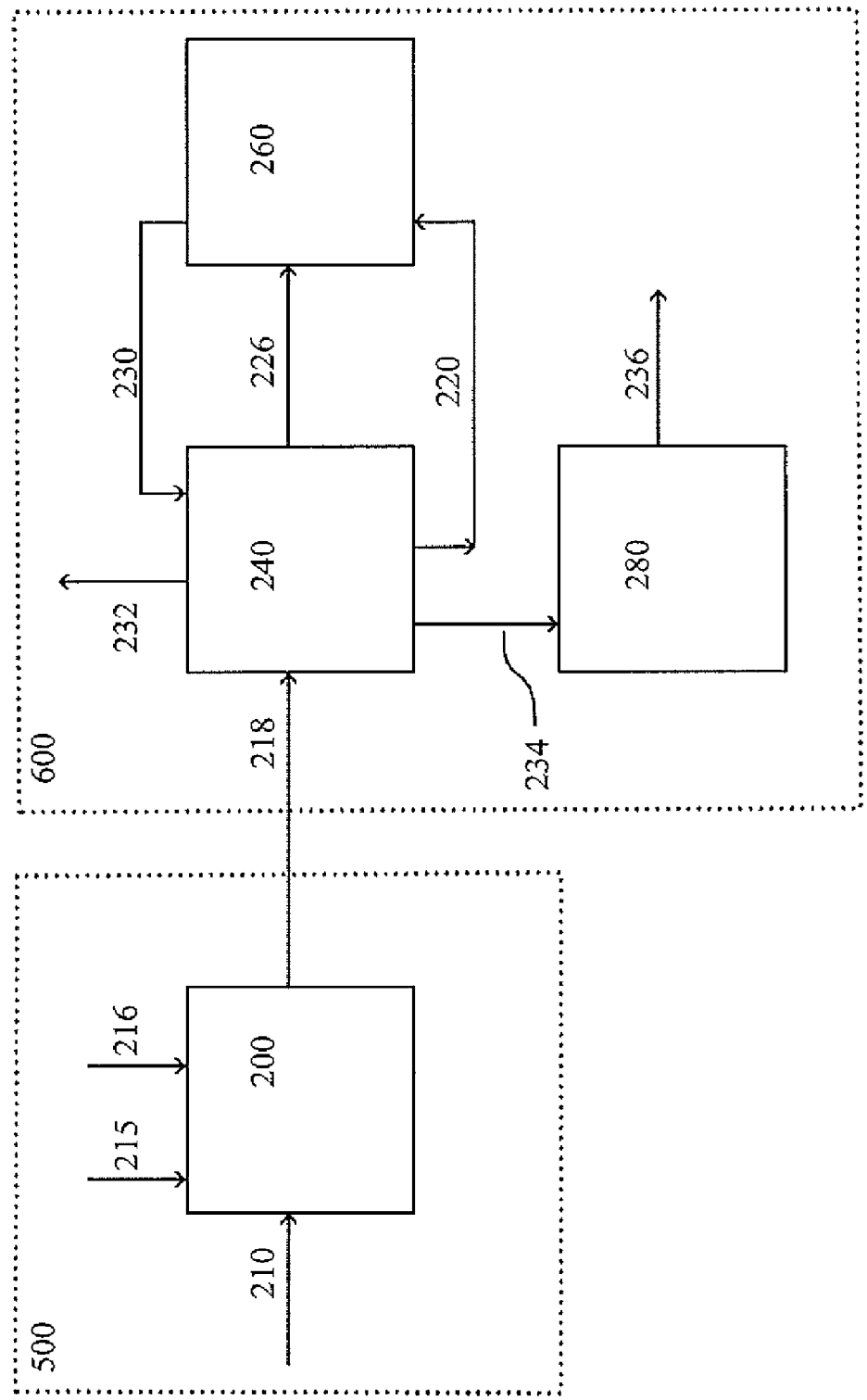

PROCESS FOR PRODUCTION OF ETHYLBENZENE FROM TOLUENE AND METHANE

CROSS-REFERENCE TO RELATED APPLICATIONS

This application is a divisional of U.S. patent application Ser. No. 12/047,953, filed Mar. 13, 2008.

BACKGROUND OF THE INVENTION

1. Field of the Invention

This invention relates generally to a process for the production of ethylbenzene and styrene.

2. Description of the Related Art

Styrene is an important monomer used in the manufacture of many of todays plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and a reduced polyalkylated content. When both alkylation and transalkylation processes are used, two separate reactors, each with its own catalyst, can be employed for each of the processes. The alkylation and transalkylation conversion processes can be carried out in the liquid phase, in the vapor phase, or under conditions in which both liquid and vapor phases are present, and combinations thereof.

In the formation of ethylbenzene from alkylation reactions of ethylene and benzene, impurities and undesirable side products may be formed in addition to the desired ethylbenzene. These undesirable products can include such compounds as xylene, cumene, n-propylbenzene and butylbenzene, as well as polyethylbenzenes, and high boiling point alkyl aromatic components, sometimes referred to as "heavies," having a boiling point at or above 185° C. As can be expected, reduction of these impurities and side products is important. This is especially true in the case of xylene, particularly the meta and para xylenes, which have boiling points that are close to that of ethylbenzene and can make product separation and purification difficult.

Ethylene is obtained predominantly from the thermal cracking of hydrocarbons, such as ethane, propane, butane, or naphtha. Ethylene can also be produced and recovered from various refinery processes. Ethylene from these sources can include a variety of undesired products, including diolefins and acetylene, which can act to reduce the effectiveness of alkylation catalysts and can be costly to separate from the ethylene. Separation methods can include, for example, extractive distillation and selective hydrogenation of the acetylene back to ethylene. Thermal cracking and separation technologies for the production of relatively pure ethylene can account for a significant portion of the total ethylbenzene production costs.

Benzene can be obtained from the hydrodealkylation of toluene which involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3+H_2 \rightarrow C_6H_6+CH_4$ This reaction requires energy input and as can be seen from the above equation, produces methane as a byproduct, which is typically separated and may used as heating fuel for the process.

In view of the above, it would be desirable to have a process of producing ethylbenzene, and styrene, which does not rely on thermal crackers and expensive separation technologies as a source of ethylene. It would also be desirable if the process was not dependent upon ethylene from refinery streams that contain impurities which can lower the effectiveness and can contaminate the alkylation catalyst. It would further be desirable to avoid the process of converting toluene to benzene with its inherent expense and loss of a carbon atom to form methane.

SUMMARY

One embodiment of the present invention is a process for making ethylbenzene which involves reacting toluene and methane in one or more reactors to form a first product stream comprising ethylbenzene and/or styrene and then further processing at least a portion of the components of the first product stream in at least a portion of an existing styrene production facility. The first product stream may also contain one or more of benzene, toluene, or methane. The process may comprise at least one separation apparatus for at least partial separation of the components from the first product stream. The reactors can include a reaction zone capable of dissipating heat to maintain the reaction zone within a desired temperature range for reacting toluene and methane to form ethylbenzene and/or styrene.

Methane may be separated from the first product stream creating a second product stream having reduced methane content. The methane may be recycled back to the reactors or may be utilized as heating fuel within the process. Toluene may also be separated from the first product stream and recycled to the reactors. At least a portion of the components of the first product stream can be further processed in a styrene production process. The styrene production process can include an alkylation reactor to form ethylbenzene by reacting benzene and ethylene, and a dehydrogenation reactor to form styrene by dehydrogenating ethylbenzene.

Yet another embodiment of the present invention is a process for making ethylbenzene and/or styrene which includes reacting toluene and methane in one or more reactors to form a first product stream comprising one or more of ethylbenzene, styrene, benzene, toluene, and methane; removing at least a portion of any methane from the first product stream to form a second product stream with reduced methane content; separation of at least a portion of the benzene from the first or second product stream; reacting at least a portion of the separated benzene in an alkylation reactor to form ethylbenzene; and dehydrogenating the ethylbenzene in one or more dehydration reactors to form styrene. At least a portion of one or more of the separation, alkylation, and dehydrogenation processes are performed utilizing the facilities of an existing styrene production facility. The one or more reactors may have one or more reaction zones and be capable of dissipating heat to maintain one or more of the reaction zones within the desired temperature range(s) to promote the reaction of toluene and methane to form ethylbenzene.

A further embodiment of the invention is a method for revamping an existing styrene production facility by adding a process for reacting toluene with methane to produce a new product stream containing ethylbenzene and styrene. The new product stream containing ethylbenzene and styrene may then be sent to the existing styrene production facility for further processing to form additional styrene. The existing styrene production facility can include a separation apparatus to remove at least a portion of any benzene and toluene from the new product stream, an alkylation reactor to form ethylbenzene by reacting the benzene and ethylene, and a dehydrogenation reactor to form styrene by dehydrogenating ethylbenzene.

BRIEF DESCRIPTION OF THE DRAWINGS

FIG. 2 is a schematic block diagram illustrating a process for making ethylbenzene and styrene according to an embodiment of the present invention.

DETAILED DESCRIPTION

Figure 1:
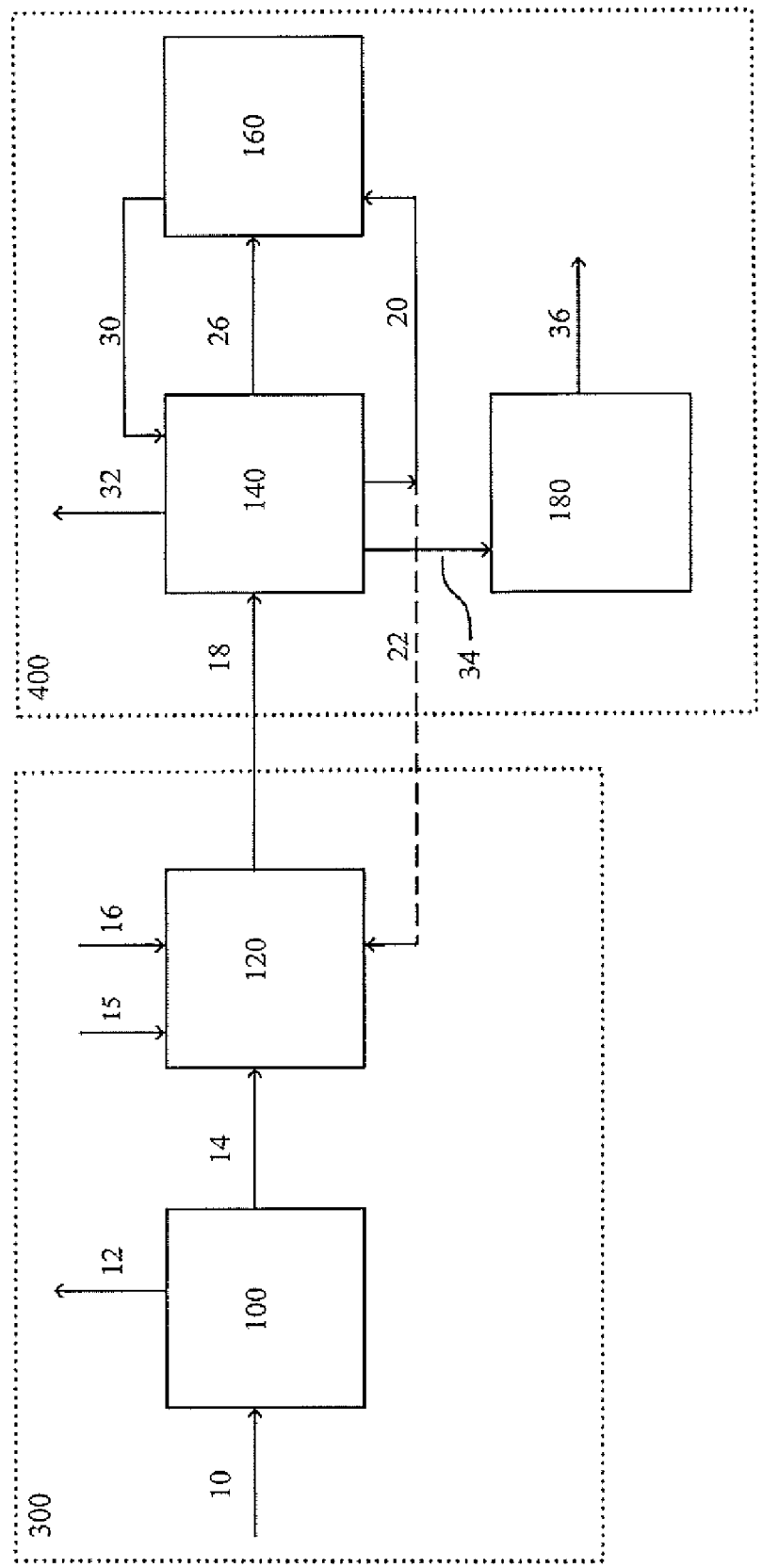
FIG. 1 is a schematic block diagram illustrating a process for making ethylbenzene and styrene.

Turning now to the drawings and referring first to FIG. 1, there is illustrated a schematic block diagram of one embodiment of an alkylation/transalkylation process carried out in accordance with the prior art. A feed stream of toluene is supplied via line 10 to reactive zone 100 which produces product streams of methane via line 12 and benzene via line 14. The benzene via line 14 along with ethylene via line 16 are supplied to an alkylation reactive zone 120 which produces ethylbenzene and other products which are sent via line 18 to a separation zone 140. The separation zone 140 can remove benzene via line 20 and send it to a transalkylation reaction zone 160. The benzene can also be partially recycled via line 22 to the alkylation reactive zone 120. The separation zone 140 can also remove polyethylbenzenes via line 26 which are sent to the transalkylation reaction zone 160 to produce a product with increased ethylbenzene content that can be sent via line 30 to the separation zone 140. Other byproducts can be removed from the separation zone 140 as shown by line 32, this can include methane and other hydrocarbons that can be recycled within the process, used as fuel gas, flared, or otherwise disposed of. Ethylbenzene can be removed from the separation zone 140 via line 34 and sent to a dehydrogenation zone 180 to produce styrene product that can be removed via line 36.

The front end of the process 300, designated by the dashed line, includes the initial toluene to benzene reactive zone 110 and the alkylation reactive zone 120. It can be seen that the input streams to the front end 300 can include toluene via line 10 and ethylene via line 16 and oxygen via line 15. There can also be input streams of benzene from alternate sources other than from a toluene reaction, shown as reactive zone 100, although they are not shown in this embodiment. The output streams include the methane via line 12 which is produced during the conversion of toluene to benzene in reactive zone 110 and the product stream containing ethylbenzene via line 18 that is sent to the back end of the process 400. The back end 400 includes the separation zone 140, the transalkylation reaction zone 160 and the dehydrogenation zone 180.

Turning now to FIG. 2, there is illustrated a schematic block diagram of one embodiment of the present invention. Feed streams of toluene supplied via line 210 and methane supplied via line 216 are supplied to a reactive zone 200, which produces ethylbenzene along with other products, which can include styrene. In some embodiments an input stream of oxygen 215 may be supplied to the reactive zone 200. The output from the reactive zone 200 includes a product containing ethylbenzene, which is supplied via line 218 to a separation zone 240. The separation zone 240 can separate benzene that may be present via line 220 which can be sent to an alkylation reaction zone 260. The alkylation reaction zone 260 can include a transalkylation zone. The separation zone 240 can also remove heavy molecules that may be present via line 226. The alkylation reaction zone 260 can produce a product with increased ethylbenzene content that can be sent via line 230 to the separation zone 240. Other byproducts can be removed from the separation zone 240 as shown by line 232, this can include methane and other hydrocarbons that can be recycled within the process, used as fuel gas, flared or otherwise disposed of. Ethylbenzene can be removed from the separation zone 240 via line 234 and sent to a dehydrogenation zone 280 to produce styrene product that can be removed via line 236. Any styrene that is produced from the reactive zone 200 can be separated in the separation zone 240 and sent to the dehydrogenation zone 280 via line 234 along with the ethylbenzene product stream, or can be separated as its own product stream, (not shown), bypassing the dehydrogenation zone 280 and added to the styrene product in line 236.

The front end of the process 500 includes the initial toluene and methane reactive zone 200. The input streams to the front end 500 are toluene via line 210 and methane via line 216 and optionally oxygen via line 215. The output stream is the product containing ethylbenzene via line 218 that is sent to the back end of the process 600. The back end 600 includes the separation zone 240, the alkylation reaction zone 260, and the dehydrogenation zone 280.

A comparison of the front end 300 of the prior art shown in FIG. 1 against the front end 500 of the embodiment of the invention shown in FIG. 2 can illustrate some of the features of the present invention. The front end 500 of the embodiment of the invention shown in FIG. 2 has a single reactive zone 200 rather than the two reactive zones contained within the front end 300 shown in FIG. 1, the reactive zone 100, and the alkylation reactive zone 120. The reduction of one reactive zone can have a potential cost savings and can simplify the operational considerations of the process.

Both front ends have an input stream of toluene, shown as lines 10 and 210. The prior art of FIG. 1 has an input stream of ethylene 16 and a byproduct stream of methane 12. The embodiment of the invention shown in FIG. 2 has an input stream of methane 216. The feed stream of ethylene 16 is replaced by the feed stream of methane 216, which is typically a lower value commodity, and should result in a cost savings. Rather than generating methane as a byproduct 12 which would have to be separated, handled and disposed of, the present invention utilizes methane as a feedstock 216 to the reaction zone 200.

A comparison of the back end 400 of the prior art shown in FIG. 1 with the back end 600 of the embodiment of the invention shown in FIG. 2 can further illustrate the features of the present invention. It can be seen that the back end 400 of the prior art shown in FIG. 1 is essentially the same as the back end 600 of the embodiment of the invention shown in FIG. 2. They each contain a separation zone, an alkylation reaction zone, a dehydrogenation zone, and are interconnected in the same or essentially the same manner. This aspect of the present invention can enable the front end of a facility to be modified in a manner consistent with the invention, while the back end remains essentially unchanged. A revamp of an existing ethylbenzene or styrene production facility can be accomplished by installing a new front end or modifying an existing front end in a manner consistent with the invention and delivering the product of the altered front end to the existing back end of the facility to complete the process in essentially the same manner as before. The ability to revamp an existing facility and convert from a toluene/ethylene feedstock to a toluene/methane feedstock by the modification of the front end of the facility while retaining the existing back end can have significant economic advantages.

The reactive zone 200 of the present invention can comprise one or more single or multi-stage reactors. In one embodiment the reactive zone 200 can have a plurality of series-connected reactors. Additionally and in the alternative the reactive zones can be arranged in a parallel manner. There can also be embodiments having multiple series-connected reactors that are arranged in a parallel manner. The reactive zone 200 can be operated at temperature and pressure conditions to enable the reaction of methane and toluene to form ethylbenzene, and at a feed rate to provide a space velocity enhancing ethylbenzene production while retarding the production of xylene or other undesirable products. The reactive zone 200 can be operated in the vapor phase. One embodiment can be operated in the vapor phase within a pressure range of atmospheric to 1000 psig. Another embodiment can be operated in the vapor phase within a pressure range of atmospheric to 500 psig. Another embodiment can be operated in the vapor phase within a pressure range of atmospheric to 300 psig. Another embodiment can be operated in the vapor phase within a pressure range of atmospheric to 150 psig.

The feed streams of methane and toluene can be supplied to the reactive zone 200 in ratios of from 2:1 moles of methane:moles of toluene to 50:1 moles of methane:moles of toluene. In one embodiment the ratios can range from 5:1 moles of methane:moles of toluene to 30:1 moles of methane:moles of toluene. The reactants, toluene and methane, can be added to the plurality of series-connected reactors in a manner to enhance ethylbenzene production while retarding the production of undesirable products. For example toluene and/or methane can be added to any of the plurality of series-connected reactors as needed to enhance ethylbenzene production.

In an embodiment of the invention oxygen is added to the reactive zone 200 in amounts that can facilitate the conversion of toluene and methane to ethylbenzene and styrene. The oxygen content can range from 1% to 50% by volume relative to the methane content. In another embodiment the desirable oxygen content can range from 2% to 30% by volume relative to the methane content. In an embodiment of the invention, the reactor of the present invention can comprise multiple reactors and oxygen can be added to the plurality of series-connected reactors in a manner to enhance ethylbenzene and/or styrene production while retarding the production of undesirable products. Oxygen can be added incrementally to each of the plurality of series-connected reactors as needed to enhance ethylbenzene and/or styrene production, to limit the exotherm from each of the reactors, to maintain the oxygen content within a certain range throughout the plurality of reactors or to customize the oxygen content throughout the plurality of reactors. In one embodiment there is the ability to have an increased or reduced oxygen content as the reaction progresses and the ethylbenzene and/or styrene fraction increases while the toluene and methane fractions decrease. There can be multiple series-connected reactors that are arranged in a parallel manner, which can increase overall production capacity and provide for auxiliary reactors to facilitate maintenance and/or regeneration activities.

The oxygen can react with a portion of the methane and result in an exothermic reaction. The heat generated by the exothermic reaction can be dissipated in many ways, such as for example utilizing an external cooling jacket, internal cooling coils, heat exchange, or by using a reactor such as a Lurgi molten salt type reactor. The heat removal can be controlled in such a manner as to maintain the reaction within a desired temperature range to facilitate the conversion of toluene and methane to ethylbenzene and/or styrene. In an embodiment, the desirable temperature range is from 550° C. to 1000° C. In another embodiment, the desirable temperature range is from 600° C. to 800° C. The heat generated by the exothermic reaction can be removed and recovered to be utilized within the process.

In one embodiment the reactive zone 200 of the present invention can comprise one or more single or multi-stage catalyst beds containing catalyst(s). The catalyst that can be used in the reactive zone 200 can include any catalyst that can couple toluene and methane to make ethylbenzene and/or styrene and are not limited to any particular type. It is believed that the oxidation reaction of toluene and methane can be accelerated by base catalysis. In one non-limiting example the catalyst can comprise one or more metal oxides. In one non-limiting example the catalyst can contain a metal oxide that is supported on an appropriate substrate. It is believed that with a metal oxide catalyst, the oxygen/oxide sites can function as the active reaction centers, which can remove hydrogen atoms from the methane to form methyl radicals and from the toluene to form benzyl radicals. The $C_8$ hydrocarbons can be formed as a result of cross-coupling between the resulting methyl and benzyl radicals. The catalysts may contain different combinations of alkali, alkaline earth, rare earth, and/or transition metal oxides. In another non-limiting example, the catalyst can comprise a modified basic zeolite. In yet another non-limiting example the catalyst can be a base zeolite, such as an X, Y, mordenite, ZSM, silicalite or AlPO4-5 that can be modified with molybdenum, sodium, or other basic ions. The zeolite catalyst may or may not contain one of more metal oxides.

The foregoing description of certain embodiments of the present invention have been presented for purposes of illustration and description. It is not intended to be exhaustive or limit the invention to the precise form disclosed, and other and further embodiments of the invention may be devised without departing from the basic scope thereof. It is intended that the scope of the invention be defined by the accompanying claims and their equivalents.

The invention claimed is:

1. A method of revamping an existing styrene production facility comprising:

providing an existing styrene production facility comprising a separation apparatus to remove at least a portion of any benzene from a first product stream, an alkylation reactor to form ethylbenzene by reacting benzene and polyethylbenzene, and a dehydrogenation reactor to form styrene by dehydrogenating ethylbenzene;

adding one or more reactors to the facility, wherein the one or more reactors are capable of reacting toluene with methane to produce a first product stream comprising ethylbenzene and styrene; wherein the one or more reaction zone comprises one or more catalyst sites comprising a catalyst selected from the group consisting of X zeolite, Y zeolite, mordenite, silicalite, and combinations thereof; and wherein the catalyst is modified with molybdenum, sodium or other basic ion.

2. The method of claim 1, further comprising sending the first product stream comprising ethylbenzene and styrene to the existing styrene production facility for further processing to form styrene.

3. The method of claim 1, wherein the first product stream further comprises one or more of benzene, toluene or methane and at least a portion of the toluene is separated from the first product stream and recycled to the one or more reactors.

4. The method of claim 1, wherein the first product stream further comprises one or more of benzene, toluene or methane and at least a portion of the methane is separated from the first product stream and recycled to the one or more reactors.

5. The method of claim 1, wherein the one or more reactors comprise a reaction zone capable of dissipating heat to maintain the reaction zone within a desired temperature range for reacting toluene and methane to form ethylbenzene and styrene.

6. The method of claim 1, wherein the first product stream further comprises methane and at least a portion of the methane is separated from the first product stream and recycled to the one or more reactors.

7. The method of claim 1, wherein the first product stream further comprises methane and at least a portion of the methane is separated from the first product stream and utilized as fuel within the process.

8. The method of claim 1, wherein the first product stream further comprises toluene and at least a portion of the toluene is separated from the first product stream and recycled to the one or more reactors.

* * * * *